US011950921B2

(12) United States Patent
Yoo et al.

(10) Patent No.: US 11,950,921 B2
(45) Date of Patent: *Apr. 9, 2024

(54) PORTABLE DEVICE FOR MEASURING SKIN CONDITION AND SKIN CONDITION DIAGNOSIS AND MANAGEMENT SYSTEM

(71) Applicant: Lululab Inc., Seoul (KR)

(72) Inventors: Sang Wook Yoo, Suwon-si (KR); Yong Joon Choe, Seoul (KR); Sijun Roh, Suwon-si (KR)

(73) Assignee: Lululab Inc., Seoul (KR)

(*) Notice: Subject to any disclaimer, the term of this patent is extended or adjusted under 35 U.S.C. 154(b) by 383 days.

This patent is subject to a terminal disclaimer.

(21) Appl. No.: 16/767,583

(22) PCT Filed: Nov. 30, 2018

(86) PCT No.: PCT/KR2018/015115
§ 371 (c)(1),
(2) Date: May 27, 2020

(87) PCT Pub. No.: WO2019/108028
PCT Pub. Date: Jun. 6, 2019

(65) Prior Publication Data
US 2020/0383629 A1    Dec. 10, 2020

(30) Foreign Application Priority Data

Nov. 30, 2017  (KR) .................... 10-2017-0162375

(51) Int. Cl.
*A61B 5/00* (2006.01)
*A61B 5/1171* (2016.01)
*G06V 40/16* (2022.01)

(52) U.S. Cl.
CPC ............ *A61B 5/442* (2013.01); *A61B 5/0013* (2013.01); *A61B 5/0077* (2013.01);
(Continued)

(58) Field of Classification Search
CPC ....... A61B 18/00; A61B 5/442; A61B 5/0013; A61B 5/0077; A61B 5/1176;
(Continued)

(56) References Cited

U.S. PATENT DOCUMENTS 11,449,997 B2 * 9/2022 Yoo .................. A61B 5/0013
2008/0147053 A1 * 6/2008 Kang .................. G01N 21/6456
600/431

(Continued)

FOREIGN PATENT DOCUMENTS

| CN | 107679466 A | * | 2/2018 | ......... G06K 9/00288 |
| CN | 107949848 A | * | 4/2018 | ......... G06K 9/00281 |

(Continued)

OTHER PUBLICATIONS

English Translation of JP 5035524 B2, 12 pages, Printed on Jun. 2, 2022 (Year: 2022).*

(Continued)

Primary Examiner — Matthew Kremer
(74) Attorney, Agent, or Firm — Revolution IP, PLLC

(57) ABSTRACT

The present invention relates to a portable device for measuring skin condition and a skin condition diagnosis and management system using same. The device for measuring skin condition according to the present invention is a portable type of device that can be easily carried by a user, and when an image of a user's face is captured, can acquire a clear image of the entire face of the user by effectively controlling the user's face position.

7 Claims, 13 Drawing Sheets

(52) U.S. Cl.
CPC .......... *A61B 5/1176* (2013.01); *A61B 5/7405* (2013.01); *A61B 5/742* (2013.01); *G06V 40/162* (2022.01); *G06V 40/168* (2022.01); *A61B 2560/0431* (2013.01)

(58) Field of Classification Search
CPC ................. A61B 5/7405; A61B 5/742; A61B 2560/0431; A61B 5/444; A61B 5/441; A61B 5/0059; G01D 5/39; G06Q 50/22; G06T 1/00; G06T 3/00; H04N 9/04; H04N 9/73; G06K 9/00; G06V 40/162; G06V 40/168; G06V 40/166
See application file for complete search history.

(56) References Cited

U.S. PATENT DOCUMENTS

| | | | | |
|---|---|---|---|---|
| 2012/0075503 | A1* | 3/2012 | Akifusa | H04N 5/2621 348/222.1 |
| 2014/0064579 | A1* | 3/2014 | Lee | G06T 7/0012 382/128 |
| 2015/0009473 | A1* | 1/2015 | Su | A61B 3/1208 351/206 |
| 2015/0124067 | A1* | 5/2015 | Bala | H04N 5/2354 348/77 |
| 2017/0119301 | A1* | 5/2017 | Kimura | G06T 7/0012 |
| 2017/0340196 | A1* | 11/2017 | Elazar | A61B 5/0022 |
| 2018/0276732 | A1* | 9/2018 | Pai | G06Q 30/0631 |

FOREIGN PATENT DOCUMENTS

| | | |
|---|---|---|
| JP | 5035524 B2 | 9/2012 |
| JP | 2013-138501 A | 7/2013 |
| KR | 10-2001-0110838 A | 12/2001 |
| KR | 10-1738417 B1 | 5/2017 |
| KR | 10-2017-0096904 A | 8/2017 |

OTHER PUBLICATIONS

English Translation of JP 2013138501B A, 17 pages, Printed on Jun. 2, 2022 (Year: 2022).*
English Translation of KR 101738417 B1, 8 pages, Printed on Jun. 2, 2022 (Year: 2022).*
Machine English Translation of KR 20170096904A, patents.google.com, 21 pages, printed out on Sep. 21, 2022. (Year: 2022).*
Machine English Translation of KR 10-2001-0110838A, patents.google.com, 5 pages, printed out on Sep. 22, 2022. (Year: 2022).*
"Compose." Merriam-Webster.com Dictionary, Merriam-Webster, https://www.merriam-webster.com/dictionary/compose. Accessed Oct. 13, 2023. (Year: 2023).*
Machine English translation of CN 107679466, Clarivate Analytics, 21 pages, printed on Oct. 17, 2023. (Year: 2023).*
Machine English translation of CN 107949848, Clarivate Analytics, 21 pages, printed on Oct. 17, 2023. (Year: 2023).*
International Search Report for PCT/KR2018/015115 dated Mar. 15, 2019 from Korean Intellectual Property Office.

* cited by examiner

[FIG. 1]
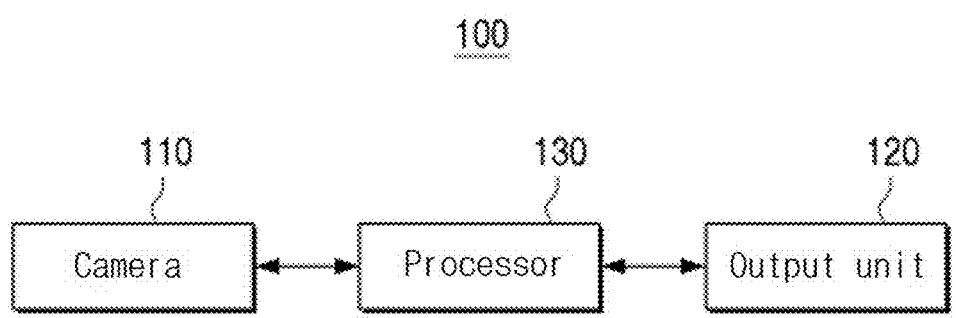
[FIG. 2]
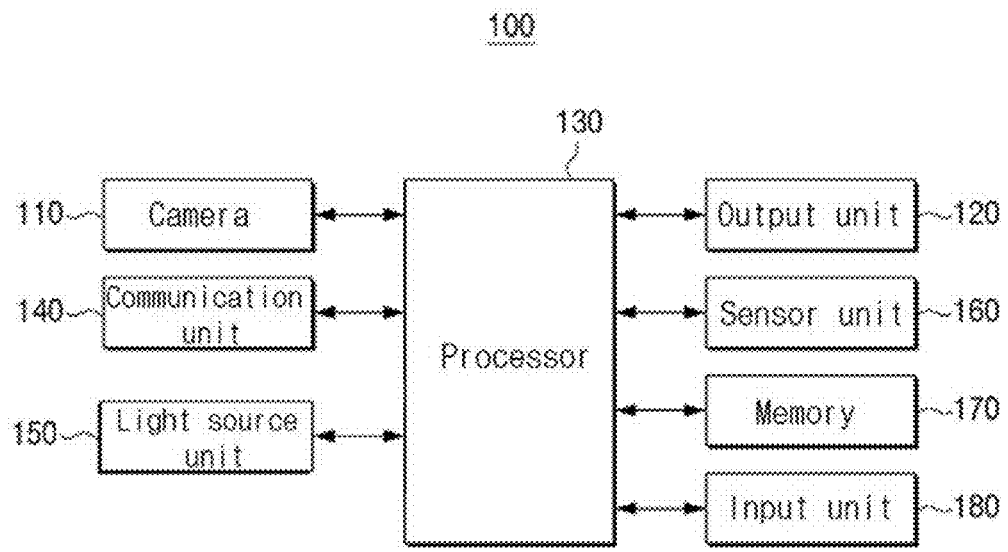

【FIG. 3】
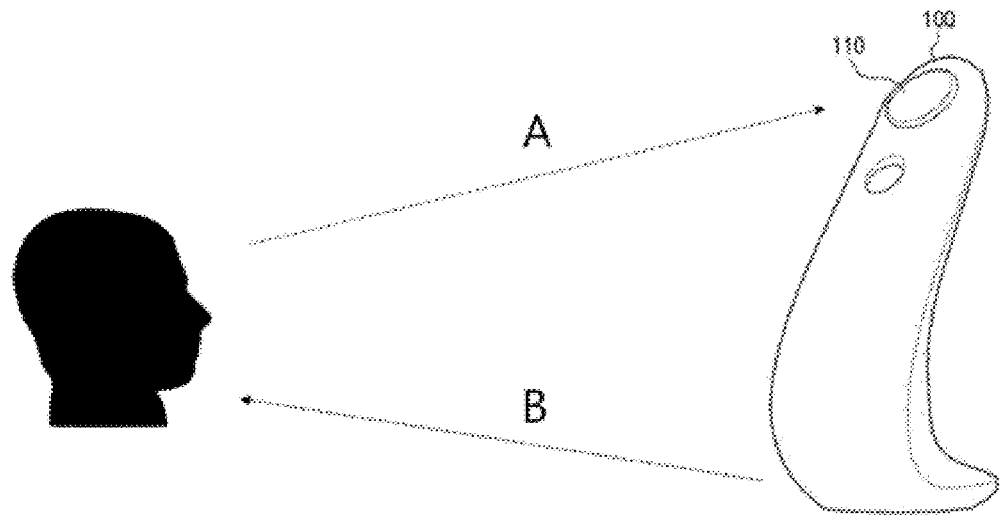
【FIG. 4】
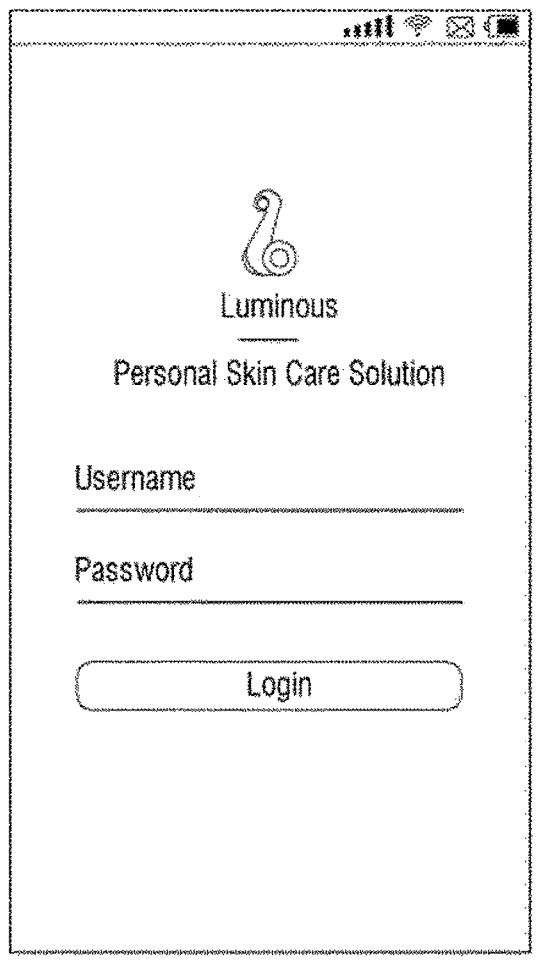

[FIG. 5]
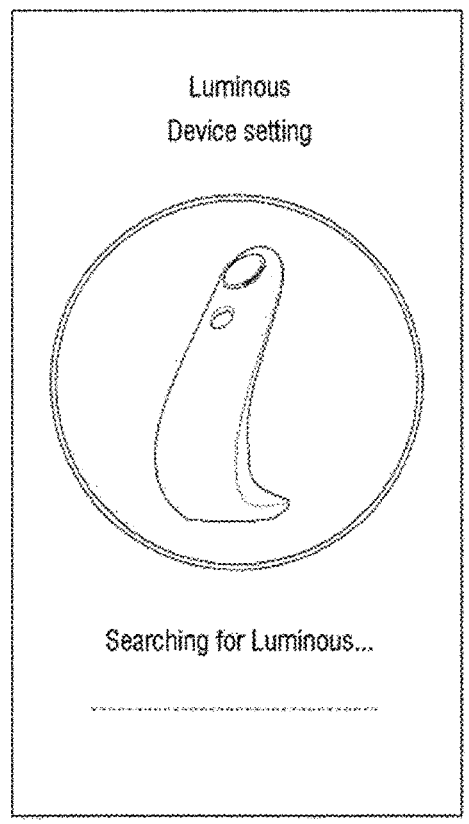
[FIG. 6]
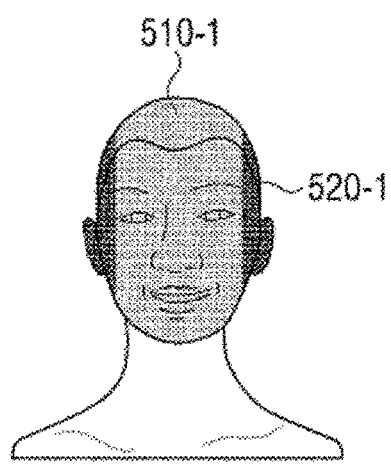

[FIG. 7]
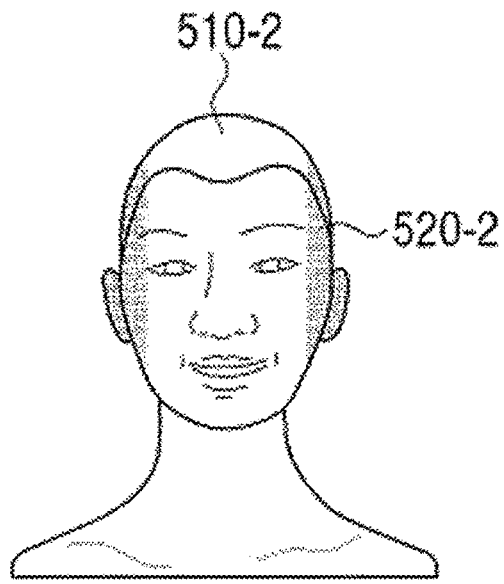
[FIG. 8]
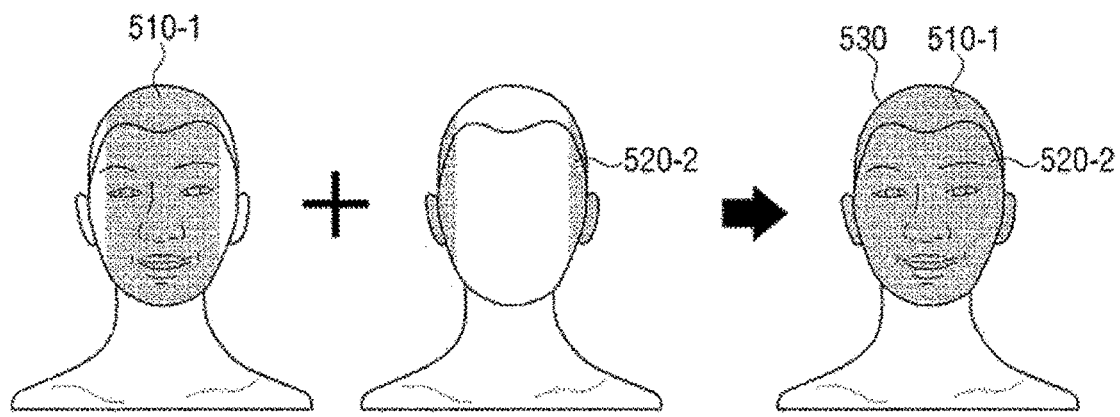

[FIG. 9]
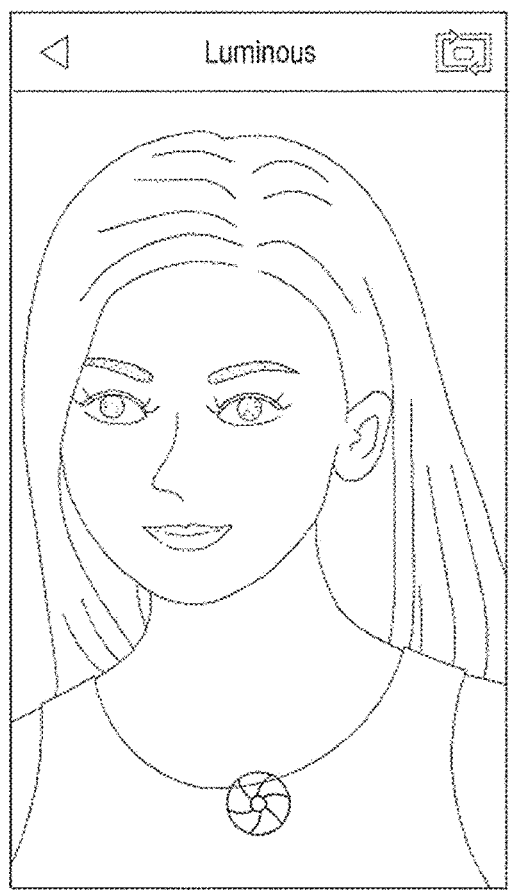

[FIG. 10]
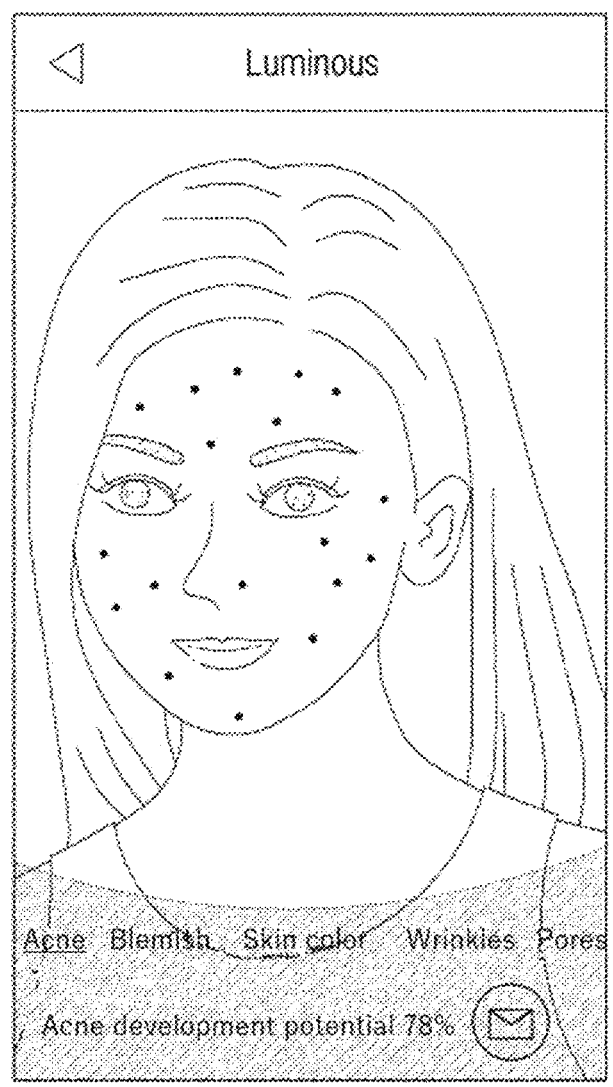

{FIG. 11}
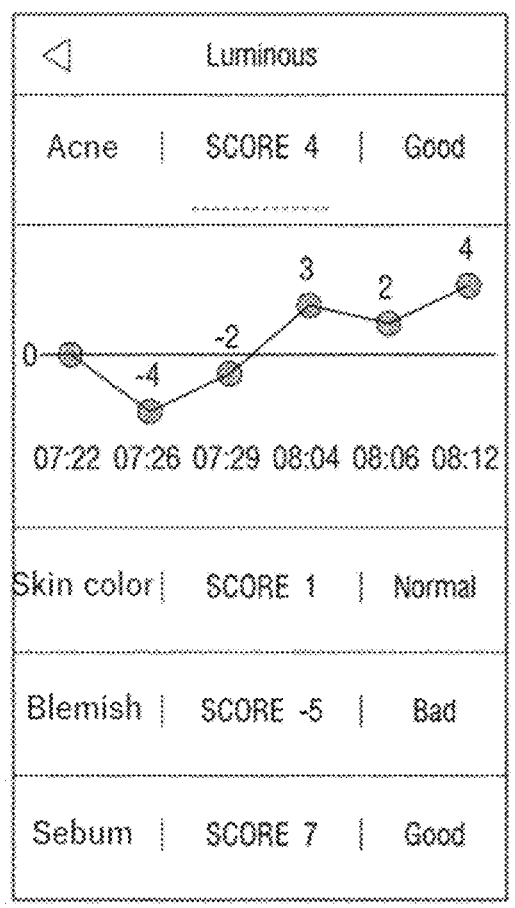

[FIG. 12]
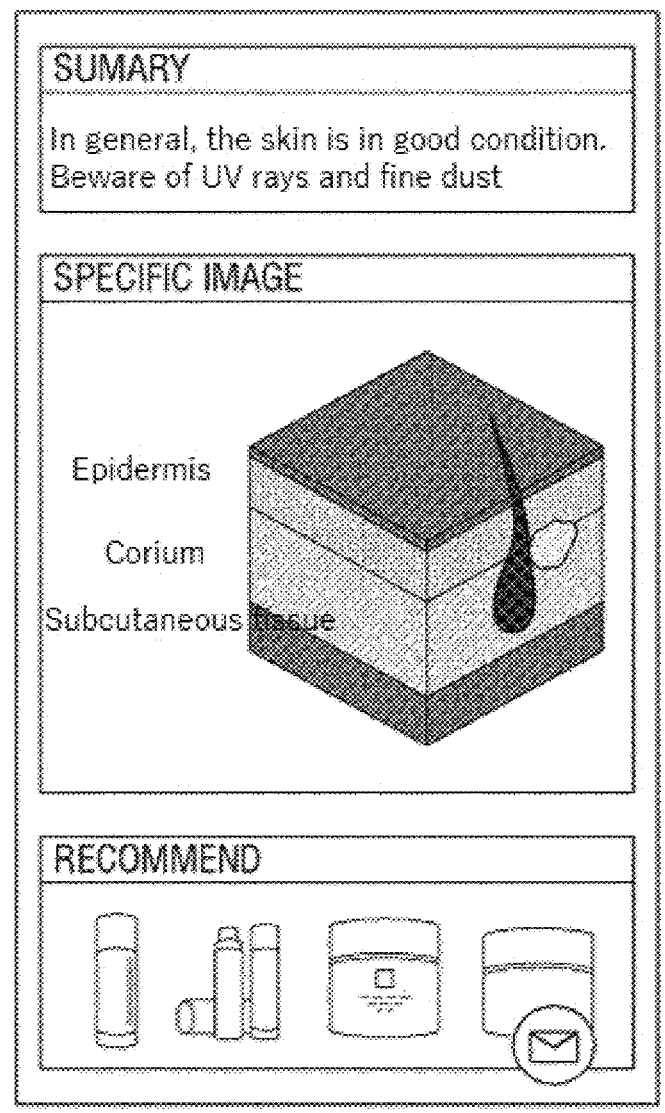

[FIG. 13]
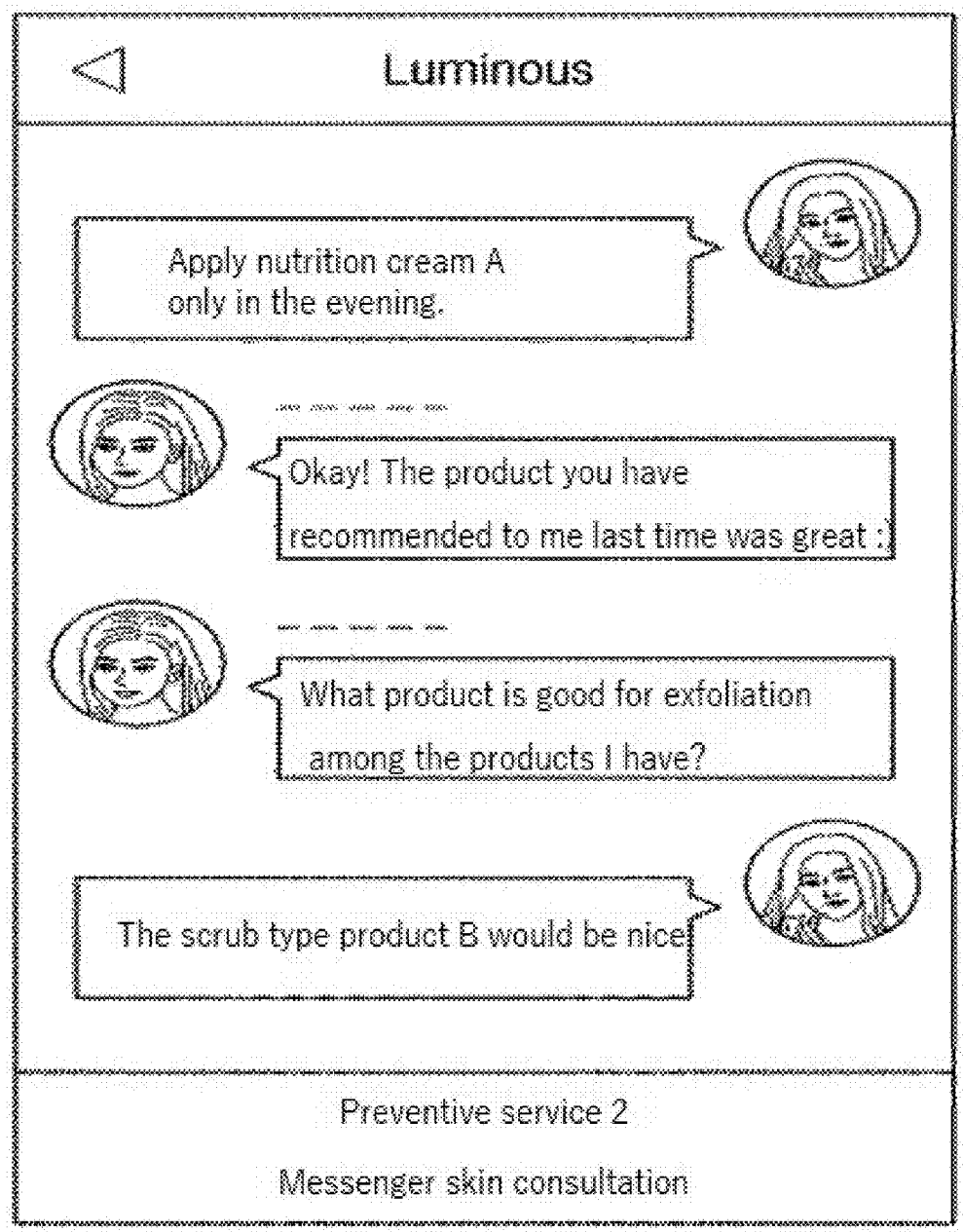

[FIG. 14]
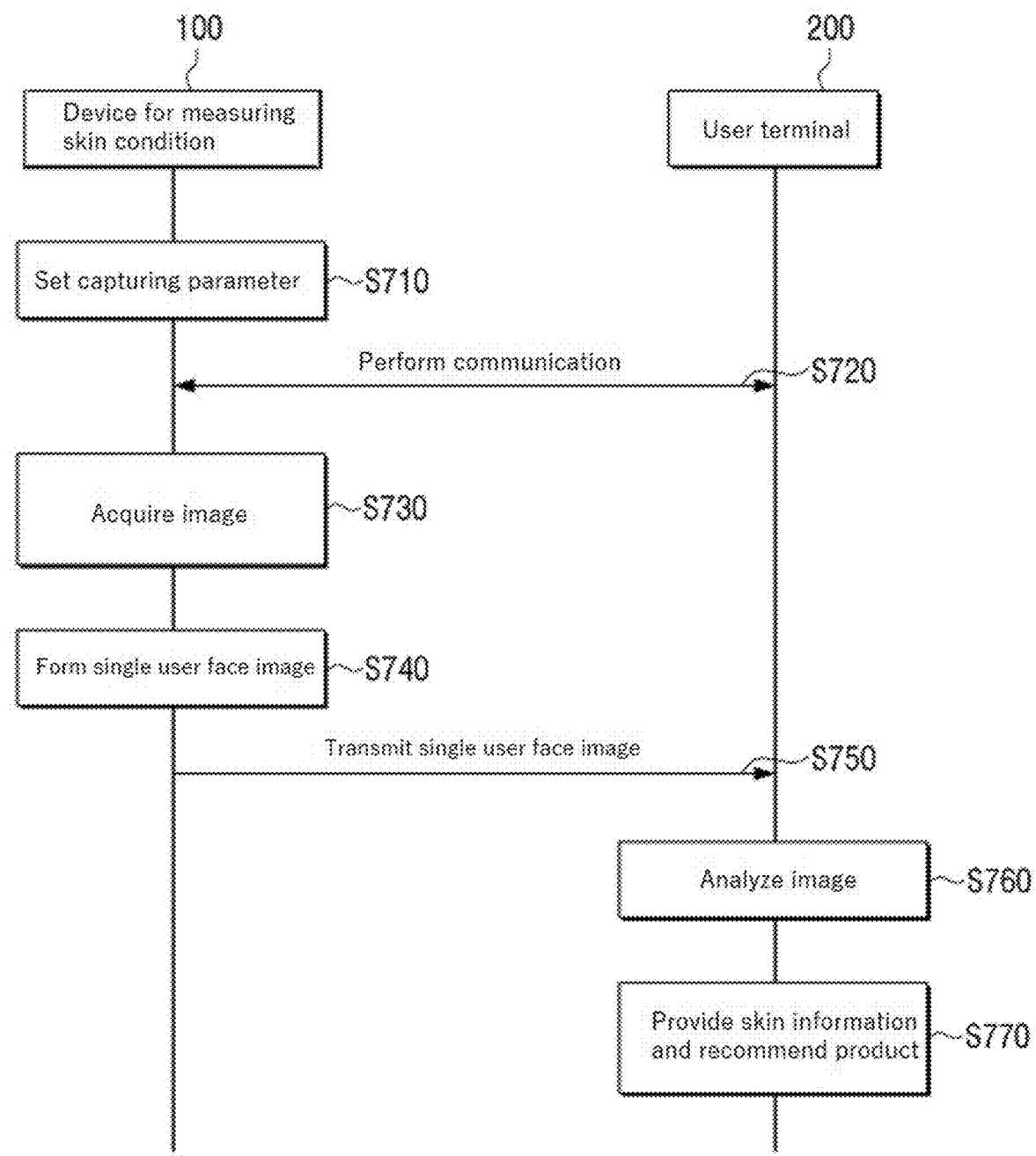

[FIG. 15]
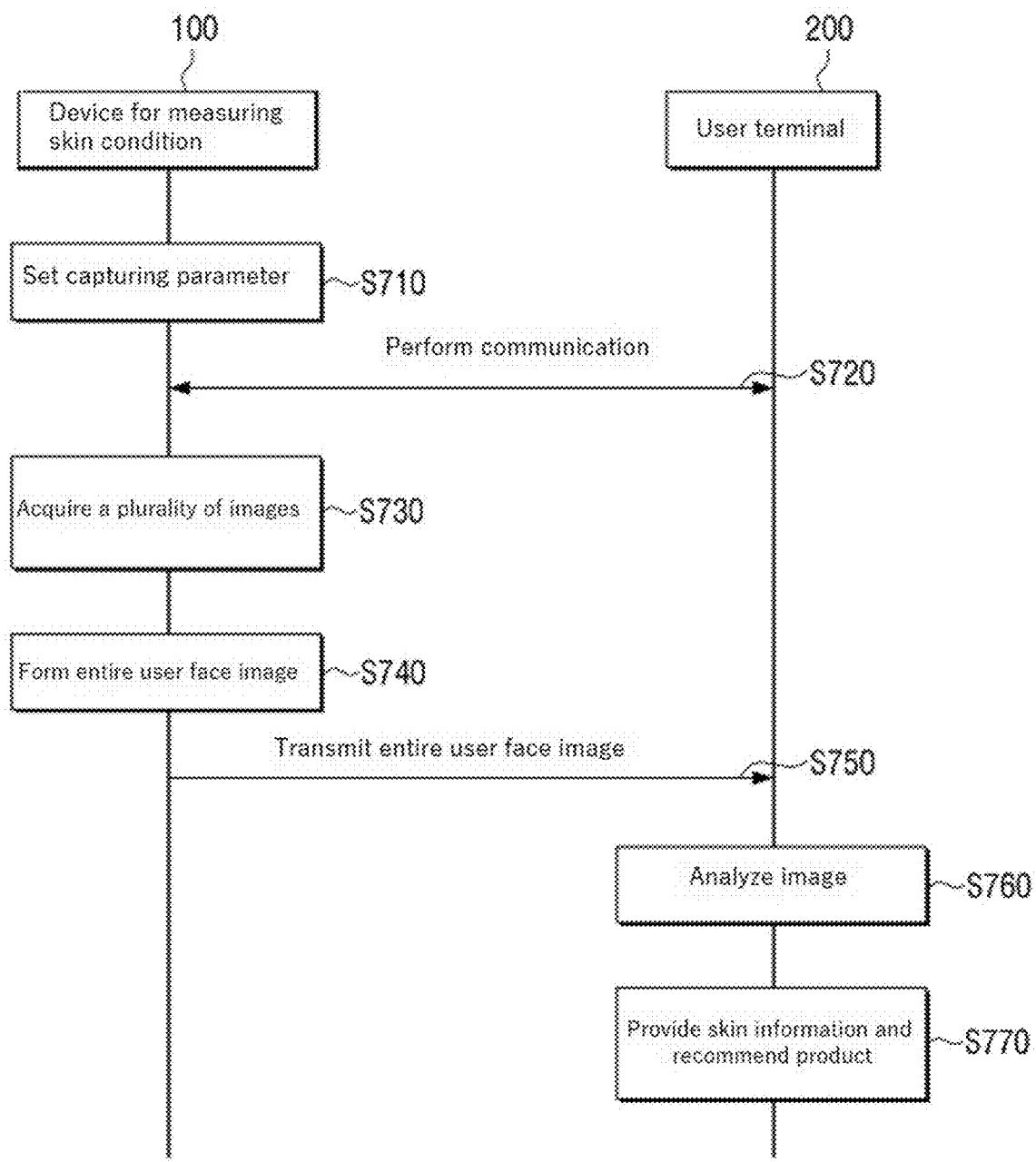

[FIG. 16]
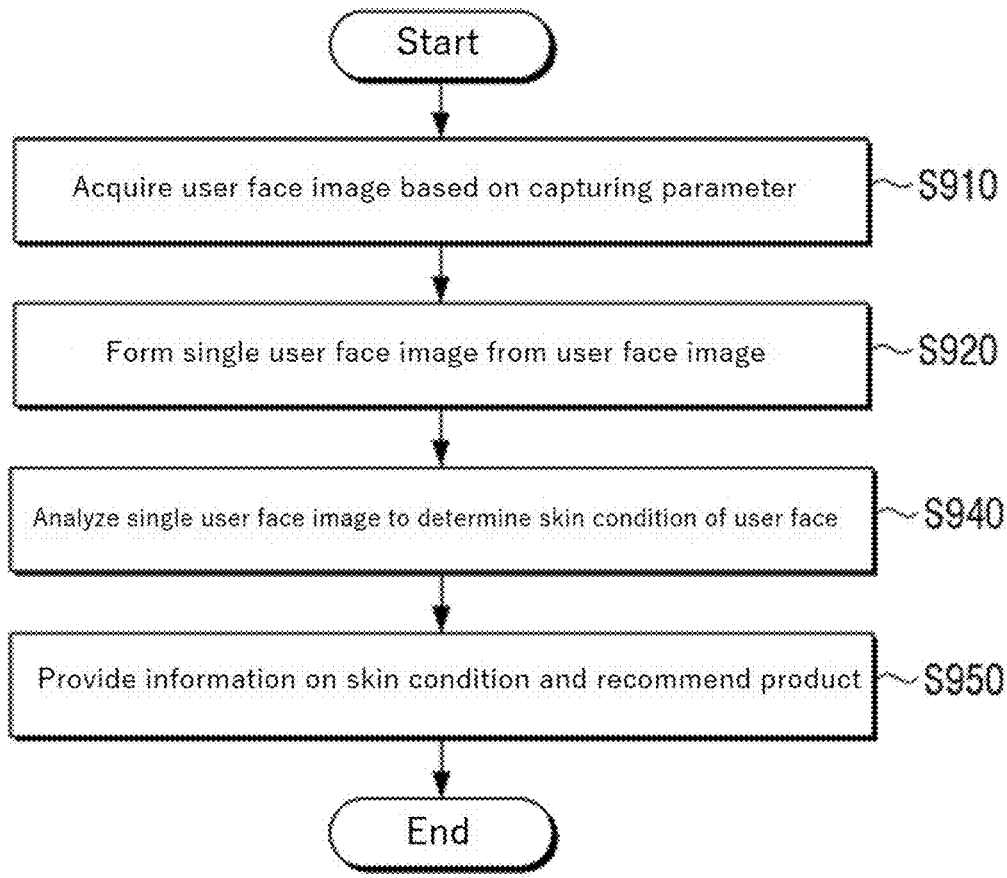

[FIG. 17]
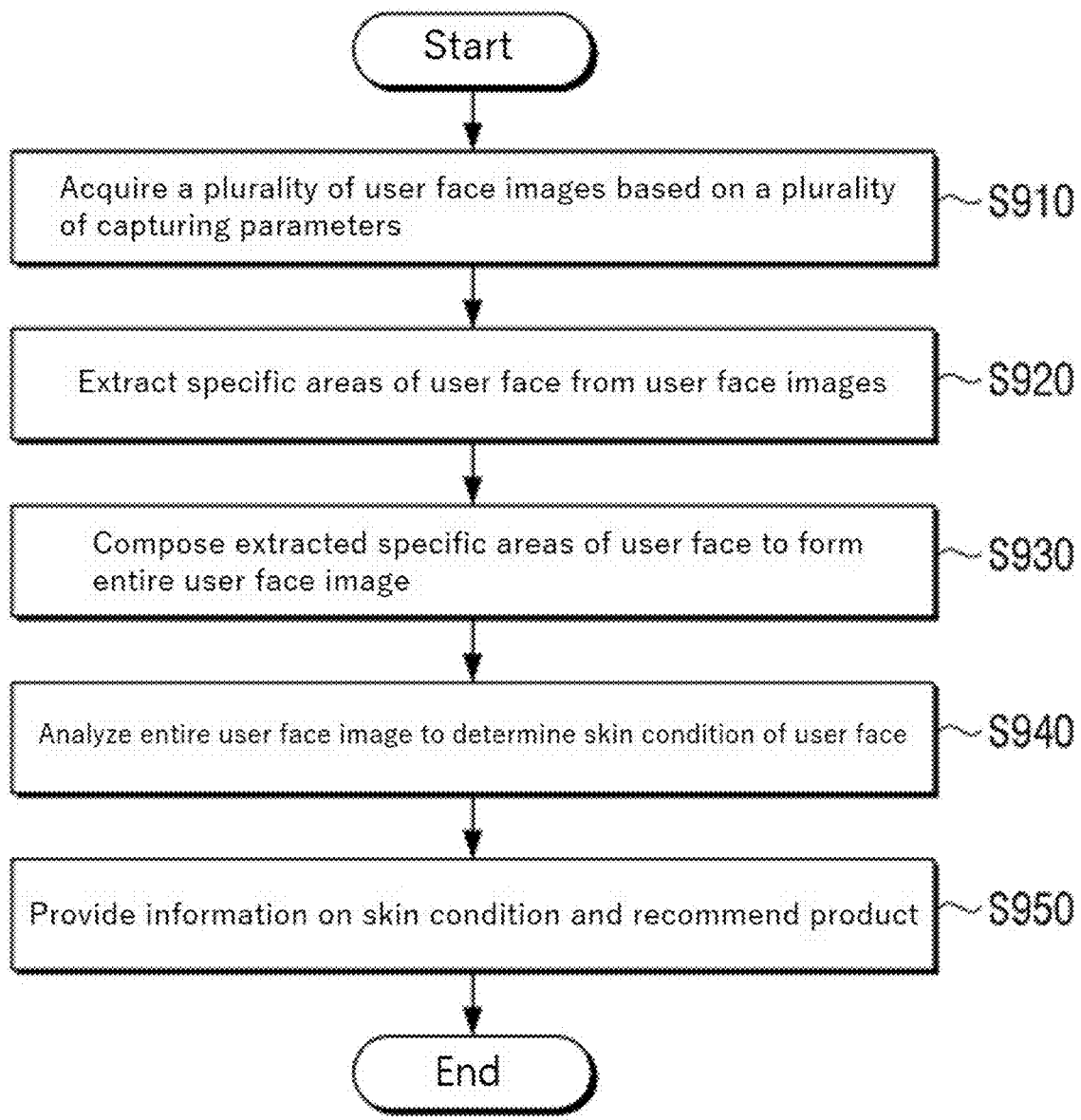

PORTABLE DEVICE FOR MEASURING SKIN CONDITION AND SKIN CONDITION DIAGNOSIS AND MANAGEMENT SYSTEM

TECHNICAL FIELD

The present invention relates to a portable device for measuring a skin condition, and a skin condition diagnosis and management system using the same.

More particularly, the present invention relates to a device for measuring a skin condition, capable of effectively controlling a user face position when an image of a user face is captured, and a skin condition diagnosis and management system using the device for measuring the skin condition.

BACKGROUND ART

Recently, as interest in beauty increases, interest in skin care of a user face is increasing. In particular, a portable device for measuring a skin condition, which captures an image of facial skin of a user to analyze various skin troubles (e.g., wrinkles, pores, acne, etc.) and the like on the user face, has been developed.

Meanwhile, a conventional device for measuring a skin condition, which is for skin analysis, captures an image of the user face based on preset capturing parameters (e.g., an intensity or a direction of a light source, an aperture value, a shutter speed, or the like) while the user face is put in the device for measuring the skin condition.

The conventional device for measuring the skin condition has an advantage that a user capturing position is fixed, but it was inconvenient in terms of portability and mobility, it was difficult to measure the skin condition in a place desired by the user, and the price was so expensive that it was difficult for general consumers to purchase the device.

Meanwhile, a portable device for measuring a skin condition, which has portability and mobility, has been developed as a skin measurement device. However, the technology development has been limited in the field of a device for measuring a specific area of skin, and a technology for analyzing an entire user face and a technology for acquiring a clear user face image to measure a skin condition still have a problem to be technically solved.

DISCLOSURE

Technical Problem

The present invention relates to a device for measuring a skin condition, which is configured in a portable type that is convenient in terms of portability, and may effectively acquire an entire face image by controlling a user face position when an image of a user face is captured.

In addition, the present invention relates to a system for diagnosing and managing a skin condition by using the device for measuring the skin condition.

Technical Solution

To achieve the objects described above, according to the present invention, there is provided a portable device for measuring a skin condition, the portable device including: a user face capturing camera; a processor for forming a single user face image for measuring the skin condition acquired by the user face capturing camera, or forming an entire user face image for measuring the skin condition by extracting specific areas of a user face from a plurality of user face images acquired based on a plurality of capturing parameters set to extract the specific areas of the user face and composing the extracted specific areas of the user face; and an output unit for suggesting a user to move a face position when a partial area of the user face deviates from the user face image acquired by the user face capturing camera, suggesting the user to move the face position when a distance between the user and the camera measured by a distance sensor for measuring the distance between the user and the camera deviates from a preset value, or suggesting the user to move the face position when the partial area of the user face deviates from the user face image acquired by the user face capturing camera and when the distance between the user and the camera measured by the distance sensor for measuring the distance between the user and the camera deviates from the preset value, wherein the processor controls the suggestion to move the face position of the output unit.

In one example, the processor may analyze brightness of a plurality of user face images acquired based on a plurality of preliminary capturing parameters to set one or more of the preliminary capturing parameters as the capturing parameters.

In one example, the processor may set a first preliminary capturing parameter, which allows a first area of the user face image to have a brightness value within a preset range, as a first capturing parameter, and may set a second preliminary capturing parameter, which allows a second area of the user face image to have a brightness value within a preset range, as a second capturing parameter.

In one example, the processor may extract a first face area from a first user face image acquired by the first capturing parameter, may extract a second face area from a second user face image acquired by the second capturing parameter, and may compose the first face area and the second face area to form the entire user face image for measuring the skin condition.

In one example, the processor may correct and compose the first face area and the second face area according to detected motion information of the portable device for measuring the skin condition.

In one example, the processor may determine a brightness difference value between the first face area and the second face area in a vicinity of a boundary between the first face area and the second face area, may determine a composition weight for at least one of the first face area and the second face area based on the brightness difference value, and may adjust brightness of at least one of the first face area and the second face area based on the composition weight to compose the first face area and the second face area.

In one example, the processor may determine a difference between an average skin color value or a skin color distribution value of the single user face image or the entire user face image acquired by the user face capturing camera and a preset average skin color value or a preset skin color distribution value of the single user face image or the entire user face image, so as to correct the average skin color value or the skin color distribution value of the single user face image or the entire user face image into the preset average skin color value or the preset skin color distribution value of the single user face image or the entire user face image.

In one example, the output unit may include a display and an audio output unit, and the display may provide a preset single user face image or a preset entire user face image to the user by overlaying the preset single user face image or the preset entire user face image.

According to the present invention, the portable device for measuring the skin condition may further include, for example, a sensor unit having the distance sensor for measuring the distance between the user and the camera, wherein the output unit may suggest the user to move the face position when the distance between the user and the camera measured by the sensor unit deviates from the preset value, and the processor may control the suggestion to move the face position of the output unit according to the distance between the user and the camera measured by the sensor unit.

According to the present invention, the portable device for measuring the skin condition may further include, for example, a communication unit for transmitting the single user face image or the entire user face image to an external user terminal. In this case, the processor may control the communication unit to transmit data for the single user face image or the entire user face image to the user terminal.

In addition, according to the present invention, there is provided a skin condition diagnosis and management system. The skin condition diagnosis and management system includes: the portable device for measuring the skin condition; and a user terminal, wherein the user terminal includes an application for analyzing a single user face image received from the portable device for measuring the skin condition, analyzing an entire user face image received from the portable device for measuring the skin condition, or analyzing the entire user face image after forming the entire user face image by extracting specific areas of a user face from a plurality of user face images received from the portable device for measuring the skin condition and composing the extracted specific areas of the user face, so as to provide a skin condition diagnosis result and recommend a product for improving the skin condition of a user based on the skin condition diagnosis result.

Advantageous Effects

According to the present invention, the portable device for measuring the skin condition is convenient in terms of portability and mobility so that the skin condition can be easily measured in a desired place.

In addition, according to the present invention, the portable device for measuring the skin condition can acquire a clear entire face image by effectively controlling the user face position when the image of the user face is captured.

Moreover, according to the present invention, the portable device for measuring the skin condition can increase accuracy of a facial skin analysis result by acquiring a face image having a uniform brightness distribution over all areas of the user face.

Furthermore, according to the present invention, the portable device for measuring the skin condition can interwork with the user terminal to diagnose the skin condition and recommend a personalized product.

However, the scope of the present invention is not limited by the above effects.

DESCRIPTION OF DRAWINGS

FIG. 1 is a block diagram schematically showing a configuration of a portable device for measuring a skin condition according to the present invention.

FIG. 2 is a block diagram showing the configuration of the portable device for measuring the skin condition according to the present invention in detail.

FIG. 3 is a view schematically showing the portable device for measuring the skin condition, which controls a user face position, according to the present invention.

FIGS. 4 to 13 are views for describing a skin condition diagnosis and management system according to one example of the present invention.

FIGS. 14 and 15 are flowcharts of the skin condition diagnosis and management system according to the present invention.

FIGS. 16 and 17 are block diagrams for describing the skin condition diagnosis and management system implemented by the device for measuring the skin condition according to the present invention.

MODE FOR INVENTION

Best Mode

Hereinafter, the present invention will be described in more detail with reference to the drawings and examples.

In the present specification, a singular expression includes a plural expression unless otherwise specified.

Although the terms used in the present specification are preferably selected from general terms that are widely used at present under the consideration of functions in the present invention, the terms may vary according to the intention of those of ordinary skill in the art, judicial precedents, or introduction of new technology. In addition, in a specific case, some terms may be arbitrarily selected by the applicant, and in this case, the meaning of the terms will be described in detail in a corresponding part of the detailed description of the invention. Therefore, the terms used in the present disclosure should be defined based on the meaning of the terms and the contents throughout the present disclosure, not by the simple names of the terms.

The present invention may have various embodiments, and the embodiments may be variously modified. Specific embodiments will be illustrated in the drawings and described in detail in the detailed description. However, it should be understood that the scope of the present invention is not limited to the specific embodiments, and includes all modifications, equivalents, or substitutes within the technical idea and technical scope of the present invention. While describing the embodiments, the detailed description of the publicly-known related art will be omitted when they are determined to make the subject matter rather unclear.

Although terms such as 'first' or 'second' may be used herein to describe various elements, the elements should not be limited by the terms. The terms are used only to distinguish one element from another element.

In the present specification, a singular expression includes a plural expression unless the context clearly indicates otherwise.

In the present specification, the term such as 'include' or 'consist of' is intended to designate the presence of characteristics, numbers, steps, operations, elements, parts, or combinations thereof disclosed herein, and shall not be construed to preclude any possibility of the presence or addition of one or more other characteristics, numbers, steps, operations, elements, parts, or combinations thereof.

In the present specification, any term including 'module' or 'unit' refers to a unit that performs at least one function or operation, and may be implemented through hardware, software, or a combination of hardware and software. In addition, a plurality of 'modules' or a plurality of 'units' may be integrated into at least one module, except for a 'module' or 'unit' which is necessary to be implemented through specific hardware, so as to be implemented as at least one processor (not shown).

Hereinafter, a portable device for measuring a skin condition according to the present invention and a method of diagnosing and managing a skin condition by using the portable device will be described in more detail with reference to the accompanying drawings.

The present invention relates to the portable device for measuring the skin condition. The device for measuring the skin condition according to the present invention is a portable device.

As used herein, the term 'portable' means that the measuring device is a mobile device that may be moved and is capable of capturing an image in a place and a position desired by a user.

Conventional devices for measuring a skin condition have been classified into a portable type and a non-portable type. In a case of a non-portable device for measuring a skin condition, there has been a difficulty in easily measuring the skin condition of the user in a place desired by the user due to a large size and a high price.

Meanwhile, in a case of a portable device for measuring a skin condition, there has been a technical difficulty in accurately acquiring a face image for recognizing the skin condition. Particularly, in a case of a device for measuring an overall skin condition, not for obtaining a diagnosis result for a local area of skin, there has been a technical difficulty in effectively acquiring an entire user face area.

Accordingly, the inventor has introduced a configuration capable of effectively acquiring an entire user face image while preventing the user face image from deviating by effectively controlling a user face position into the device for measuring the skin condition. Therefore, the device for measuring the skin condition according to the present invention may be portable, and may effectively acquire the entire user face image while preventing the deviation. Ultimately, the device for measuring the skin condition according to the present invention may clearly diagnose the skin condition of the user.

FIG. 1 is a block diagram schematically showing a configuration of a portable device for measuring a skin condition according to the present invention.

As shown in FIG. 1, a portable device 100 for measuring a skin condition according to the present invention may include a user face capturing camera 110, an output unit 120, and a processor 130.

The user face capturing camera 110 according to the present invention may capture an image of a user face.

In detail, the camera 110 may acquire a user face image by capturing the image of the user face based on an arbitrary capturing parameter.

The user face image acquired by the camera 110 may be, for example, a user face image for forming a single user face image or a plurality of user face images for forming an entire user face image, which will be described below.

As used herein, the term "single user face image" refers to a single image acquired by the camera 110 for analyzing the skin condition and formed by the processor 130, and the term is used herein in order to differentiate the single user face image from the entire user face image which is formed through a technology for extracting and composing specific areas of the user face images acquired based on a plurality of capturing parameters.

Meanwhile, as used herein, the term "entire user face image" refers to a user face image which is formed through a technology for extracting specific face areas from the user face images acquired based on the capturing parameters and composing the specific face areas, and used to measure the skin condition.

In one example, the camera 110 may acquire the user face image by capturing the image of the user face based on the arbitrary capturing parameter. In this case, the user face image may be formed as the single user face image by the processor 130.

In another example, the camera 110 may acquire a plurality of images by capturing images of the user face based on the capturing parameters.

In more detail, the camera may acquire a plurality of images by capturing the images of the user face a plurality of times based on different capturing parameters (an intensity of a light source unit, a shutter speed value, an aperture value, or the like).

The portable device for measuring the skin condition according to the present invention may include the processor 130. The processor 130 may control an overall operation of each component in the portable device for measuring the skin condition.

As shown in FIGS. 1 and 2, each of individual components of the portable device for measuring the skin condition according to the present invention may be controlled and operated by the processor 130. In particular, the processor 130 may control an overall operation of the portable device 100 for measuring the skin condition by using various programs stored in a memory 170 that will be described below.

Among various control operations, the processor 130 may especially set acquisition of the single user face image or acquisition of the entire user face image.

In other words, the processor 130 may form the single user face image for measuring the skin condition acquired by the user face capturing camera, or form the entire user face image for measuring the skin condition by extracting the specific areas of the user face from the user face images acquired based on the capturing parameters set to extract the specific areas of the user face and composing the extracted specific areas of the user face.

The capturing parameters for analyzing facial skin of the user may be set by the processor 130. The capturing parameter may include, for example, one or more of an intensity of a light source unit provided in the portable device for measuring the skin condition, a direction of the light source unit, a shutter speed, and an aperture value, and may be set differently for each user.

In one example, the processor 130 may analyze brightness of a user face image acquired based on a preliminary capturing parameter to set the preliminary capturing parameter as the capturing parameter. At this time, the preliminary capturing parameter may be determined according to an external lighting environment. In this case, the processor 130 may acquire a user face image based on a capturing parameter set based on the preliminary capturing parameter, and may set the user face image as the single user face image for measuring the skin condition.

Hereinafter, a control operation of the processor 130 for extracting specific areas of the user face based on a plurality of preliminary capturing parameters and composing the specific areas to form the entire user face image for measuring the skin condition will be described in more detail.

The processor 130 may analyze brightness of a plurality of user face images acquired based on a plurality of preliminary capturing parameters to set one or more of the preliminary capturing parameters as the capturing parameters.

In one example, when the image captured based on the first preliminary capturing parameter among the preliminary capturing parameters has a brightness value within a preset range in the first area (e.g., a face center area) of the user face, the processor 130 may set the first preliminary capturing parameter as the first capturing parameter corresponding to the first area of the user face. In addition, when the image captured based on the second preliminary capturing parameter among the preliminary capturing parameters has a brightness value within a preset range in the second area (e.g., a face outer periphery area) of the user face, the processor 130 may set the second preliminary capturing parameter as the second capturing parameter corresponding to the second area of the user face.

In other words, the processor 130 may set the first preliminary capturing parameter, which allows the first area of the user face image to have a brightness value within the preset range, as the first capturing parameter, and may set the second preliminary capturing parameter, which allows the second area of the user face image to have a brightness value within the preset range, as the second capturing parameter.

After the capturing parameters are set, the processor 130 may extract the specific areas of the user face from the user face images acquired based on the set capturing parameters.

In one example, the processor 130 may acquire a first user face image by capturing the image of the user face based on the first capturing parameter, and may acquire a second user face image by capturing the image of the user face based on the second capturing parameter. In addition, the processor 130 may extract user face areas corresponding to the images from the images, and may compose the extracted user face areas to acquire the entire user face image.

In other words, the processor 130 may extract the first face area from the first user face image acquired by the first capturing parameter, and may extract the second face area from the second user face image acquired by the second capturing parameter. In addition, the processor 130 may compose the first face area and the second face area to form the entire user face image for measuring the skin condition.

In this case, the processor 130 may correct and compose the first face area and the second face area according to detected motion information of a portable skin diagnosis device. In other words, when a motion of the portable device 100 for measuring the skin condition is detected while capturing the second user face image, the processor 130 may correct the second face area according to the detected motion of the device. According to another embodiment, the processor 130 may correct the second user face image before extracting the second face area according to the motion of the portable device 100 for measuring the skin condition. The detection of the motion may be, for example, performed by a sensor unit 160 that will be described below.

In addition, when composing the first face area and the second face area, the processor 130 may perform brightness correction to compose the first face area and the second face area.

In detail, the processor 130 may determine a brightness difference value between the first face area and the second face area in the vicinity of a boundary between the first face area and the second face area. In addition, the processor 130 may determine a composition weight for at least one of the first face area and the second face area based on the brightness difference value. In this case, the composition weight may be a weight for adjusting the brightness. Further, the processor 130 may adjust brightness of at least one of the first face area and the second face area based on the composition weight to compose the first face area and the second face area.

In addition, in order to solve a reproducibility deterioration problem in a skin condition diagnosis and management system due to a variation of an average skin color value or a skin color distribution of the single user face image or the entire user face image for each image capturing operation, the processor 130 may correct the average skin color value or a skin color distribution value into a preset value. In other words, the processor 130 corrects the average skin color value or the skin color distribution value of the single user face image or the entire user face image, which varies for each image capturing operation, into the preset value by a white balance function of the camera, so that the reproducibility deterioration problem for measuring the skin condition can be solved.

In one example, the processor 130 may determine a difference between the average skin color value or the skin color distribution value of the single user face image or the entire user face image acquired by the camera 110 and a preset average skin color value or a preset skin color distribution value of the single user face image or the entire user face image, so as to correct the average skin color value or the skin color distribution value of the single user face image or the entire user face image into the preset average skin color value or the preset skin color distribution value.

The correction of the differences between the skin color values or the skin color distribution values may be, for example, performed by using an image processing technology such as histogram matching, but the embodiments are not limited thereto.

Meanwhile, the preset average skin color value or the preset skin color distribution value of the single user face image or the entire user face image may be stored in a server or a memory unit 170 that will be described below, and may be an average skin color value or a skin color distribution value of the single user face image or the entire user face image acquired by the camera through a previous image capturing operation.

The portable device for measuring the skin condition according to the present invention may include the output unit 120. The output unit 120 may suggest the user to move a face position when a partial area of the user face deviates from the user face image acquired by the user face capturing camera, may suggest the user to move the face position when a distance between the user and the camera measured by a distance sensor for measuring the distance between the user and the camera deviates from a preset value, or may suggest the user to move the face position when the partial area of the user face deviates from the user face image acquired by the user face capturing camera and when the distance between the user and the camera measured by the distance sensor for measuring the distance between the user and the camera deviates from the preset value. In this case, as shown in FIG. 2, the processor 130 may control the suggestion for the user to move the face position of the output unit 120.

The portable device for measuring the skin condition according to the present invention can effectively acquire the entire user face image through the configuration of the output unit 120 that performs the suggestion for the user to move the face position.

The suggestion for the user to move the face position may be performed when the partial area of the user face deviates from the user face image acquired by the user face capturing camera and/or when the distance between the user and the camera measured by the distance sensor for measuring the distance between the user and the camera deviates from the preset value.

In one example, the suggestion for the user to move the face position by the output unit 120 may be performed when the partial area of the user face deviates from the user face image acquired by the user face capturing camera.

In the above description, a deviation degree of the user face area may be, for example, determined based on data stored in a sensing module stored in the memory 170 controlled by the processor 130.

In more detail, the deviation degree of the user face area may be determined based on a case in which detection of a face outer periphery of the user fails or the face outer periphery is cut off at the boundary when the face outer periphery of the user is detected from the user face image. In this case, the face outer periphery may be acquired through a landmark detection technology, an edge detection technology, or the like.

In another example, the suggestion for the user to move the face position by the output unit 120 may be performed when the distance between the user and the camera measured by the distance sensor for measuring the distance between the user and the camera deviates from the preset value.

Meanwhile, the distance between the user and the camera may be measured by the distance sensor. The distance sensor may be, for example, included in the sensor unit 160.

Therefore, the portable device 100 for measuring the skin condition according to the present invention may further include a sensor unit 160 having the distance sensor for measuring the distance between the user and the camera. In this case, the output unit 120 may suggest the user to move the face position when the distance between the user and the camera measured by the sensor unit 160 deviates from the preset value, and the processor 130 may control the suggestion to move the face position of the output unit 120 according to the distance between the user and the camera 110 measured by the sensor unit 160.

In a specific example, the sensor unit 160 may include the distance sensor to measure the distance between the user and the camera, and may link a measurement result with the sensing module of the memory 170 that will be described below to control the suggestion to move the face position by the processor 130 and to perform the suggestion to move the face position by the output unit 120.

Meanwhile, the sensor unit 160 may detect an external lighting device to determine the preliminary capturing parameters including: an intensity and a direction of the light source unit; and the shutter speed, the aperture value, an exposure value, and the like of the camera, and may serve to detect the motion information of the device for measuring the skin condition as described above.

The distance sensor of the sensor unit 160 may include an ultrasonic sensor or a time-of-flight (ToF) sensor.

In addition to the distance sensor, the sensor unit 160 may further include a motion sensor (e.g., an acceleration sensor, a gyro sensor, an electromagnetic sensor, etc.) for detecting the motion of the portable device 100 for measuring the skin condition.

In another example, the suggestion for the user to move the face position by the output unit 120 may be performed in the above two cases, specifically, in the case when the partial area of the user face deviates from the user face image acquired by the user face capturing camera, and the case when the distance between the user and the camera measured by the distance sensor for measuring the distance between the user and the camera deviates from the preset value.

As described above, through the configuration including: the sensor unit 160 having the distance sensor; the memory 170; the output unit 120; and the processor 130 for controlling the sensor unit 160, the memory 170, and the output unit 120, acquisition of an inaccurate face image due to the deviation of the user can be prevented in advance, and a clear user face image can be acquired.

The output unit 120 may perform the suggestion for the user to move the face position. In one example, the output unit 120 may include a display and an audio output unit, and the suggestion to move the face position may be performed by the display and/or the audio output unit.

In another example, the display of the output unit 120 may suggest the user to move the face position based on the image of the user which is previously captured.

In detail, the display of the output unit 120 may suggest the user to move the face position based on a preset single user face image or a preset entire user face image.

In more detail, the display of the output unit 120 may provide the preset single user face image or the preset entire user face image to the user by overlaying the preset single user face image or the preset entire user face image so as to suggest the user to move the face position. In the above description, the preset single user face image or the preset entire user face image may be acquired by the user face capturing camera, and refers to a previously-captured user face image stored in the memory unit 170 or the server.

Meanwhile, the display may display various image data and a user interface (UI) in addition to the suggestion to move the face position.

The audio output unit of the output unit 120 may, for example, perform the suggestion to move the face position through a voice. The audio output unit may output various notification sounds or voice messages in addition to the suggestion to move the face position.

In another example, the suggestion to move the face position of the output unit 120 may be performed by an arrow indicating a preferred direction to move the face position or a light emitting diode (LED) implementing a specific color.

FIG. 3 is a view schematically showing the portable device for measuring the skin condition, which controls a user face position, according to the present invention.

As shown in FIG. 3, the portable device for measuring the skin condition according to the present invention may (A) determine a deviation state of the user face area in real time from a real-time streaming image obtained through the camera under the control of the processor 130 and (B) suggest to move the face position according to the determined deviation state, and/or may (A) measure the distance between the user and the camera 110 by the sensor unit 160 having the distance sensor and (B) suggest to move the face position according to the measured distance. In this case, the suggestion to move the face position may be implemented through a voice, an image, an LED, or the like.

The portable device for measuring the skin condition according to the present invention may further include a light source unit 150. The light source unit 150 may include at least one light source, and the light source may provide light toward the user face. In this case, the light source may be, for example, designed to emit at least one of red light, green light, and blue light so as to emit white light from the light source unit 150. Meanwhile, the light source unit 150 may provide different intensities under the control of the processor 130.

Meanwhile, the portable device for measuring the skin condition according to the present invention may autonomously analyze the single user face image or the entire user face image formed by the processor 130.

In addition, after the single user face image or the entire user face image formed by the processor 130 is transmitted to a user terminal 200, the single user face image or the entire user face image may be analyzed through the user terminal 200. In this case, the portable device for measuring the skin condition may further include a communication unit 140.

In other words, the portable device for measuring the skin condition according to the present invention may further include a communication unit 140 for transmitting the single user face image or the entire user face image to an external user terminal. In this case, the processor 130 may control the communication unit 140 to transmit data for the single user face image or the entire user face image to the user terminal 200.

The communication unit 140 may, for example, receive a request to capture the image of the user face from the external user terminal 200, and may transmit the single user face image or the entire user face image to the external user terminal 200. In this case, the communication unit 140 may be implemented as a Bluetooth module, which is only an example, but may be implemented as various communication modules such as a ZigBee communication module, a Wi-Fi communication module, or an NFC communication module.

Meanwhile, in the above embodiment, the portable device for measuring the skin condition has been described as transmitting the single user face image or the entire user face image to the external user terminal 200, which is only an example, but may transmit the user face images acquired based on the capturing parameters to the external user terminal 200. In this case, the user terminal 200 may analyze the skin condition of the user face by extracting and composing the specific face areas of the user face images in the same manner as an operation performed by the processor 130 as described above.

In addition, the processor 130 may directly analyze the single user face image or the entire user face image to acquire skin condition information on at least one of pigmentation, acne, sebum, pores, and wrinkles on the user face, and may output the acquired skin condition information through the output unit 120.

The portable device for measuring the skin condition according to the present invention may further include a memory 170. The memory 170 may store various modules for driving the portable device 100 for measuring the skin condition.

For example, the memory 170 may store software including a base module, a sensing module, a communication module, a presentation module, a web browser module, and a service module. In this case, the base module refers to a basic module for processing a signal received from hardware included in the portable device 100 for measuring the skin condition to transmit the processed signal to an upper layer module. The sensing module refers to a module for collecting information from various sensors and analyzing and managing the collected information, and may include a face recognition module, a distance measurement module, a voice recognition module, a motion recognition module, and the like. The presentation module refers to a module for configuring a display screen, and may include a multimedia module for reproducing and outputting multimedia contents, a UI, and a UI rendering module for performing graphic processing. The communication module refers to a module for performing communication with an outside. The web browser module refers to a module for accessing a web server by performing web browsing. The service module refers to a module including various applications for providing various services.

As described above, the memory 170 may include various program modules, but the various program modules may be partially omitted, modified, or added depending on a type and characteristics of the portable device 100 for measuring the skin condition.

In addition, the memory 170 may store the capturing parameters for each user.

Meanwhile, the memory 170 may be implemented as a non-volatile memory, a volatile memory, a flash memory, a hard disk drive (HDD), a solid state drive (SSD), or the like. The memory 170 may be accessed by the processor 130, and read/write/modify/delete/update of data may be performed by the processor 130.

In addition, the portable device for measuring the skin condition according to the present invention may further include an input unit 180. The input unit 180 may receive a user command to operate the portable device 100 for measuring the skin condition to transmit information on the user command to the processor 130. In particular, the input unit 180 may be a button (e.g., a button for tacking a photograph, etc.) provided on the portable device 100 for measuring the skin condition, which is only an example, but may be implemented through other input devices.

As one embodiment of the present disclosure, the input unit 180 may be implemented as a touch panel for detecting a touch of the user, a (digital) pen sensor, or the like. As a touch panel, for example, at least one of a capacitive type touch panel, a pressure-sensitive type touch panel, an infrared touch panel, and an ultrasonic type touch panel may be used. In addition, the touch panel may further include a control circuit. However, it is only an example that the input unit 180 is implemented as the touch panel, the pen sensor, or the like, so that the input unit 180 may be implemented as a microphone for receiving a speech of the user, a pointing device, or the like.

In addition, the present invention relates to a skin condition diagnosis and management system using a portable device for measuring a skin condition.

The skin condition diagnosis and management system may include a portable device 100 for measuring a skin condition and a user terminal 200.

The portable device 100 for measuring the skin condition may include, as described above, a camera 110, an output unit 120, and a processor 130. In addition, the portable device 100 for measuring the skin condition may include, as described above, a communication unit 140, a light source unit 150, a sensor unit 160, a memory 170, and an input unit 180.

The user terminal 200 may include an application (hereinafter referred to as "skin analysis application") for analyzing the single user face image received from the portable device for measuring the skin condition, analyzing the entire user face image received from the portable device for measuring the skin condition, or analyzing the entire user face image after forming the entire user face image by extracting the specific face areas of the user face from the user face images received from the portable device for measuring the skin condition and composing the extracted specific areas of the user face, so as to provide a skin condition diagnosis result and recommend a product for improving the skin condition of the user based on the skin condition diagnosis result.

The skin condition diagnosis and management system according to the present invention may include the portable device 100 for measuring the skin condition. In addition, the portable device 100 for measuring the skin condition may include the processor 130. An operation of interworking, by the processor 130, with the external user terminal 200 to provide information on the skin condition of the user face will be described in detail with reference to FIGS. 4 to 13.

In FIG. 4, a start screen of the skin analysis application included in the user terminal 200 is displayed. The start screen of the skin analysis application may include a UI for user login. The skin analysis application may be executed in response to a user command, and when the user login is performed, the user terminal 200 may search for an external, communicable and portable device 100 for measuring a skin condition. In this case, as shown in FIG. 5, the user terminal 200 may display a screen for guiding the search for the external and portable device 100 for measuring the skin condition.

When the external and portable device 100 for measuring the skin condition is retrieved, the user terminal 200 may communicate with the external and portable device 100 for measuring the skin condition. In this case, the user terminal 200 may perform communication with the portable device 100 for measuring the skin condition through Bluetooth communication or Wi-Fi communication. When the communication between the user terminal 200 and the portable device 100 for measuring the skin condition is established, the user terminal 200 may transmit information on a logged-in user to the portable device 100 for measuring the skin condition.

The processor 130 of the portable device 100 for measuring the skin condition may determine whether the capturing parameter for the logged-in is preset. When the capturing parameter corresponding to the logged-in user has not been preset, the processor 130 may analyze the brightness of the user face image acquired based on the preliminary capturing parameter to set the preliminary capturing parameter as the capturing parameter.

The processor 130 may acquire the user face image by capturing the image of the user face based on the capturing parameter through the user face capturing camera 110. The user face image may be transmitted to the user terminal through the communication unit 140 of the portable device 100 for measuring the skin condition so as to be used as the single user face image for analyzing the skin condition.

Hereinafter, an operation of acquiring the entire user face image by extracting the specific areas of the user face from the user face images acquired based on the preliminary capturing parameters and the capturing parameters and composing the extracted specific areas will be described in more detail.

The processor 130 of the portable device 100 for measuring the skin condition may determine whether the capturing parameters for the logged-in user are preset. When the capturing parameters corresponding to the logged-in user have not been preset, the processor 130 may analyze brightness of the user face images acquired based on the preliminary capturing parameters to set one or more of the preliminary capturing parameters as the capturing parameters.

The processor 130 may acquire the images by capturing the images of the user face based on the preliminary capturing parameters through the user face capturing camera 110.

For example, the processor 130 may acquire first to nth images by capturing the images of the user face based on first to nth preliminary capturing parameters. In this case, the preliminary capturing parameters may include: the intensity and the direction of the light source unit 150; and the shutter speed, the aperture value, the exposure value, and the like of the camera 110, and the values may be determined according to the external lighting device detected by the sensor unit 160.

When the image captured based on the first preliminary capturing parameter among the preliminary capturing parameters has a brightness value within a preset range with respect to a center area of the user face, the processor 130 may set the first preliminary capturing parameter as a first capturing parameter corresponding to the center area of the user face. In addition, when the image captured based on the second preliminary capturing parameter among the preliminary capturing parameters has a brightness value within a preset range with respect to an outer periphery area of the user face, the processor 130 may set the second preliminary capturing parameter as a second capturing parameter corresponding to the outer periphery area of the user face. In other words, the processor 130 may set the preliminary capturing parameters having optimal brightness values in the center area and the outer periphery area of the user face as the capturing parameters corresponding to the respective areas.

Meanwhile, in the above embodiment, the user face is divided into two areas (e.g., the center area and the outer periphery area), which is only an example, but the user face may be divided into three or more areas to set capturing parameters corresponding to respective areas.

In addition, the processor 130 may acquire the images by capturing the images of the user face based on a plurality of preset capturing parameters through the user face capturing camera 110. For example, the processor 130 may acquire the first user face image captured by using the first capturing parameter and the second user face image captured by using the second capturing parameter. In this case, as shown in FIG. 6, the first user face image may include a center area 510-1 having a brightness value within a first range and an outer periphery area 520-1 having a brightness value within a second range, and as shown in FIG. 7, the second user face image may include a center area 510-2 having a brightness value within a third range and an outer periphery area 520-2 having a brightness value within a fourth range. In this case, a section in which the first range and the fourth range overlap each other may exist. In other words, the first range and the fourth range may have identical or similar brightness values.

In addition, the processor 130 may extract corresponding user face areas from the user face images, and may compose the extracted areas to generate the entire user face image.

In detail, as shown in FIG. 8, the processor 130 may extract the center area 510-1 from the first user face image, may extract the outer periphery area 520-2 from the second user face image, and may compose the center area 510-1 and the outer periphery area 520-2 to generate an entire user face image 530. In this case, the entire user face image 530 may have a uniform brightness value over all as shown in FIG. 8.

Meanwhile, according to the present invention, the suggestion to move the user face controlled by the processor 130 and implemented by the output unit 120 may be performed before acquiring of the user face image based on the preliminary capturing parameter, or before acquiring of the user face images based on the preliminary capturing parameters and acquiring of the user face images based on the capturing parameters.

The processor 130 may control the communication unit 140 to transmit the single user face image or the entire user face image for measuring the skin condition to the external user terminal 200.

As shown in FIG. 9, the application of the user terminal 200 may display the received single user face image or the received entire user face image.

In addition, the application of the user terminal 200 may provide a skin condition diagnosis result for the user face based on the single user face image or the entire user face image.

As one embodiment of the present invention, the application of the user terminal 200 may separate the single user face image or the entire user face image into a melanin image and a hemoglobin image by using a pigment separation technology. In addition, the application may acquire information on a blemish degree and a skin tone by analyzing the melanin image, and acquire information on erythema existing on the user face by analyzing the hemoglobin image.

In addition, as another embodiment of the present invention, the application of the user terminal 200 may acquire information on acne (e.g., acne occurrence, probability of acne occurrence, etc.) existing on the user face by analyzing RGB of the single user face image or the entire user face image.

Further, as another embodiment of the present invention, the application of the user terminal 200 may acquire information on sebum existing on the user face from a UV image of the single user face image or the entire user face image.

Moreover, as another embodiment of the present invention, the application of the user terminal 200 may acquire information on pores (e.g., presence of pores, a depth of the pore, etc.) existing on the user face by analyzing RGB of the single user face image or the entire user face image.

In addition, as another embodiment of the present invention, the application of the user terminal 200 may acquire information on wrinkles (e.g., presence of wrinkles, a depth of the wrinkle, etc.) existing on the user face by analyzing RGB of the single user face image or the entire user face image.

Further, the application of the user terminal 200 may output acquired information on the skin condition of the user face. For example, as shown in FIG. 10, the application of the user terminal 200 may display a UI that visually provides the information on the skin condition.

Furthermore, as shown in FIG. 11, the application of the user terminal 200 may display a UI including history information about the analyzed skin condition.

In addition, as shown in FIG. 12, the application of the user terminal 200 may display a UI that provides skin trouble prevention information and information on a recommended cosmetic product.

In other words, the application may recommend a product for improving the skin condition of the user based on the skin condition diagnosis result.

In addition, as shown in FIG. 13, the application of the user terminal 200 may provide a chat service with a skin counselor.

FIGS. 14 and 15 are sequence diagrams for the skin condition diagnosis and management system using the device for measuring the skin condition according to the present invention.

FIG. 14 is a sequence diagram for a system for forming a single user face image and diagnosing and managing a skin condition based on the single user face image, and FIG. 15 is a sequence diagram for a system for forming an entire user face image and diagnosing and managing a skin condition based on the entire user face image.

In detail, the portable device 100 for measuring the skin condition may set a capturing parameter or a plurality of capturing parameters (S710). In this case, the portable device 100 for measuring the skin condition may set a plurality of preliminary capturing parameters for acquiring images having an optimal brightness value for each area of a user face among the preliminary capturing parameters as the capturing parameters.

Then, the portable device 100 for measuring the skin condition and the user terminal 200 may communicate with each other (S720). Meanwhile, in another embodiment of the present invention, step S710 may be performed after step S720.

Thereafter, the portable device 100 for measuring the skin condition may acquire a user face image or a plurality of images by capturing an image of the user face based on the capturing parameter or the capturing parameters (S730).

Then, the portable device 100 for measuring the skin condition may generate a single user face image or an entire user face image (S740). In detail, the portable device 100 for measuring the skin condition may form a user face image acquired based on the set capturing parameter as the single user face image, or may generate the entire user face image by extracting user face areas corresponding to the images acquired by the capturing parameters and composing the extracted user face areas.

Thereafter, the portable device 100 for measuring the skin condition may transmit the single user face image or the entire user face image to the user terminal 200 (S750).

Then, the user terminal 200 may analyze the single user face image or the entire user face image (S760). In particular, the user terminal 200 may acquire information (e.g., acne, a color tone, wrinkles, etc.) on the skin condition of the user face by analyzing the single user face image or the entire user face image.

Thereafter, the user terminal 200 may provide information on the skin condition of the user face and a recommendation on a product for improving the skin condition (S770).

Meanwhile, according to the present invention, real-time determination (A) of the processor 130 for the suggestion (B) to move the user face according to a deviation state of the user face or the suggestion (B) to move the user face according to distance measurement, which is controlled by the processor 130 and implemented by the output unit 120, may be performed before step S710 and before step S730.

Meanwhile, since the device for measuring the skin condition may also perform the functions of diagnosing the skin condition and providing the information as described above, the description thereof will be given in detail below.

FIGS. 16 and 17 are block diagrams for describing that the skin condition diagnosis and management system is implemented by the device for measuring the skin condition according to the present invention.

Since steps S910 to S930 shown in FIGS. 16 and 17 are duplicative elements corresponding to the elements of the skin condition diagnosis and management system described above, the detailed description thereof will be omitted.

The portable device 100 for measuring the skin condition may determine the skin condition of the user face by analyzing the single user face image or the composed entire user face image (S940). In detail, the portable device 100 for measuring the skin condition may analyze the single user face image or the synthesized entire user face image to acquire information on various skin conditions such as a skin tone as well as skin troubles (e.g., acne, pores, wrinkles, etc.) of the user face.

In addition, the portable device 100 for measuring the skin condition may provide information on the determined skin condition (S950). In this case, the portable device 100 for measuring the skin condition may visually provide information and services on the skin condition through various UIs as shown in FIGS. 9 to 13, which is only an example, but may provide the information on the skin condition in an audible form.

The methods described above may be implemented in the form of program instructions that can be executed through various computer devices, and may be recorded on a computer-readable medium. The computer-readable medium may include program instructions, data files, data structures, and the like alone or in combination. The program instructions recorded on the medium may be specially designed and configured for the present invention, or may be known and available to those skilled in the art of computer software. Examples of a computer-readable recording medium include: magnetic media such as hard disks, floppy disks, and magnetic tapes; optical recording media such as CD-ROMs and DVDs; magneto-optical media such as floptical disks; and hardware devices that are specially configured to store and execute program instructions, such as ROMs, RAMs, and flash memories. Examples of the program instructions include high-level language codes that can be executed by a computer using an interpreter or the like as well as machine language codes generated by a compiler. The hardware devices may be configured to operate as one or more software modules to perform the operations of the present invention, and vice versa.

According to various embodiments of the present invention as described above, a clear entire user face image is acquired while preventing the user face from deviating, so that accuracy of a facial skin analysis result can be increased. In addition, since it is unnecessary to insert the user face into the device for measuring the skin condition, a convenience in terms of portability and mobility can be improved.

As described above, although the present disclosure has been described with limited embodiments and drawings, the present disclosure is not limited to the above embodiments, and various changes and modifications can be made from the above description by those skilled in the art to which the present disclosure pertains. Therefore, the scope of the present disclosure should not be limited to the above-described embodiments, but should be defined by the appended claims and their equivalents.

The invention claimed is:

1. A portable device for measuring a skin condition, the portable device comprising:
a user face capturing camera;
a processor for forming an entire user face image for measuring the skin condition by
setting a plurality of capturing parameters,
acquiring a plurality of user face images based on the plurality of capturing parameters, the plurality of user face images being captured by the user face capturing camera, wherein the plurality of capturing parameters includes a first capturing parameter and a second capturing parameter based on any one or more of an intensity of a light source, a shutter speed value, and an aperture value,
extracting specific areas of a user face from each of the plurality of user face images, and
gathering the extracted specific areas of the user face from each of the plurality of user face images;
a sensor unit having a distance sensor for measuring a distance between the user and the user face capturing camera; and
an output unit for suggesting the user to move a face position when a partial area of the user face deviates from a reference frame in which the user face capturing camera acquires the plurality of user face images, suggesting the user to move the face position when the distance between the user and the user face capturing camera, which is measured by the distance sensor for measuring the distance between the user and the user face capturing camera, deviates from a preset value, or suggesting the user to move the face position when the partial area of the user face deviates from the reference frame in which the user face capturing camera acquires the plurality of user face images, and the distance between the user and the user face capturing camera, which is measured by the distance sensor for measuring the distance between the user and the user face capturing camera, deviates from the preset value,
wherein the processor controls the output unit for suggesting the user to move the face position,
wherein, in the plurality of capturing parameters,
the first capturing parameter acquires a first user face image of the plurality of user face images, and
the second capturing parameter acquires a second user face image of the plurality of user face images,
the first user face image including
a first center area of the user face having a first brightness value within a first range, and
a first outer periphery area of the user face having a second brightness value within a second range,
the second user face image including
a second center area of the user face having a third brightness value within a third range, and
a second outer periphery area of the user face having a fourth brightness value within a fourth range,
wherein the processor extracts the specific areas including the first center area from the first user face image of the plurality of user face images and the second outer periphery area from the second user face image of the plurality of user face images, and gathers the first center area and the second outer periphery area to generate the entire user face image having a uniform brightness value.

2. The portable device of claim 1, wherein the processor corrects and gathers the first center area and the first outer periphery area and the second center area and the second outer periphery area according to detected motion information of the portable device for measuring the skin condition.

3. The portable device of claim 1, wherein the processor determines a brightness difference value between the first center area and the second outer periphery area in a vicinity of a boundary, determines a composition weight for at least one of the first center area and the second outer periphery area based on the brightness difference value, and adjusts brightness of at least one of the first center area and the second outer periphery area based on the composition weight.

4. The portable device of claim 1, wherein the processor determines a difference between an average skin color value or a skin color distribution value of the first and second user face images and a preset average skin color value or a preset skin color distribution value of the first and second user face images or the entire user face image, so as to correct the average skin color value or the skin color distribution value of the first and second user face images based on the preset average skin color value or the preset skin color distribution value of the first and second user face images.

5. The portable device of claim 1, wherein the output unit includes a display and an audio output unit, and
the display provides a preset entire user face image to the user.

6. The portable device of claim 1, further comprising a communication unit for transmitting the first and second user face images or the entire user face image to an external user terminal,
wherein the processor controls the communication unit to transmit data for the first and second user face images or the entire user face image to the user terminal.

7. A skin condition diagnosis and management system comprising:
the portable device for measuring the skin condition according to claim 1; and
a user terminal,
wherein the user terminal includes an application for analyzing the entire user face image after forming the entire user face image by extracting the specific areas of the user face from the plurality of user face images received from the portable device for measuring the skin condition and gathering the extracted specific areas of the user face, so as to provide a skin condition diagnosis result and recommend a product for improving the skin condition of the user based on the skin condition diagnosis result.

* * * * *